United States Patent [19]

Allen

[11] Patent Number: 5,325,543
[45] Date of Patent: Jul. 5, 1994

[54] UNDERGARMENT WITH A POCKET FOR RELEASABLY SECURING AN ABSORBENT PAD

[76] Inventor: Tanya R. Allen, 18984 Fairfield, Detroit, Mich. 48221

[21] Appl. No.: 919,981

[22] Filed: Jul. 27, 1992

Related U.S. Application Data

[63] Continuation of Ser. No. 653,623, Jan. 11, 1991.

[51] Int. Cl.$^5$ .............................................. A41B 9/12
[52] U.S. Cl. ..................................... 2/406; 2/400; 604/396; 604/387; 604/385.2
[58] Field of Search ................... 2/400, 402, 403, 405, 2/406; 450/89, 102, 104, 103, 106; 604/396, 397

[56] References Cited

U.S. PATENT DOCUMENTS

| | | | |
|---|---|---|---|
| 2,012,879 | 8/1936 | Kneibler | 2/403 |
| 2,058,970 | 10/1936 | Flesh | 2/403 X |
| 2,078,184 | 4/1937 | Russell | 2/403 X |
| 2,206,412 | 7/1940 | Levy | 2/406 X |
| 2,342,187 | 2/1944 | Gardner | 2/400 |
| 2,468,445 | 4/1949 | Hurst | 2/406 |
| 2,493,113 | 1/1950 | Dance | 2/406 X |
| 2,532,029 | 11/1950 | Medoff | 604/397 X |
| 2,566,844 | 9/1951 | Laughead | 2/70 |
| 2,591,079 | 4/1952 | Leaton | 2/402 X |
| 2,748,772 | 6/1956 | Titone et al. | 2/406 X |
| 2,771,881 | 11/1956 | Betts | 2/402 |
| 2,881,447 | 4/1959 | Shackelford | 2/49 R |
| 2,985,170 | 9/1957 | Title | . |
| 3,171,773 | 3/1965 | Estes et al. | 604/397 X |
| 3,237,625 | 3/1966 | Johnson | 2/406 |
| 3,424,162 | 1/1969 | Parravicini | 2/400 X |
| 3,489,149 | 1/1970 | Larson | 2/406 |
| 3,599,638 | 8/1971 | Rickard | 2/406 |
| 3,819,401 | 6/1974 | Massengale et al. | 2/406 X |
| 3,828,367 | 8/1974 | Bourgeois | 2/402 |
| 3,828,785 | 8/1974 | Gamm et al. | 604/397 X |
| 4,044,769 | 8/1977 | Papajohn | . |
| 4,241,462 | 12/1980 | Tagawa et al. | 2/406 |
| 4,326,302 | 4/1982 | Lowe et al. | 2/405 |
| 4,560,381 | 12/1985 | Southwell | 2/406 X |
| 4,641,381 | 2/1987 | Heran et al. | . |
| 4,642,819 | 2/1987 | Ales et al. | . |
| 4,646,362 | 3/1987 | Heran et al. | . |
| 4,674,135 | 6/1987 | Greene | . |
| 4,695,279 | 9/1987 | Steer | 604/397 X |
| 4,718,902 | 1/1988 | Bonito | 604/396 |
| 4,743,239 | 5/1988 | Cole | 604/396 X |
| 4,928,323 | 5/1990 | Nathan | . |
| 5,105,473 | 4/1992 | Valtakari | 2/24 X |

FOREIGN PATENT DOCUMENTS

| | | | |
|---|---|---|---|
| 281513 | 4/1966 | Australia | 2/406 |
| 800567 | 10/1950 | Fed. Rep. of Germany | 2/406 |
| 226626 | 9/1962 | Fed. Rep. of Germany | 2/406 |
| 236315 | 3/1964 | Fed. Rep. of Germany | 2/406 |
| 2356948 | 5/1975 | Fed. Rep. of Germany | 2/406 |
| 1189649 | 10/1959 | France | 604/396 |
| 1226117 | 7/1960 | France | 2/406 |
| 1229456 | 9/1960 | France | 604/396 |
| 2608023 | 6/1988 | France | 2/400 |
| 1144674 | 3/1969 | United Kingdom | 2/406 |
| 2176692 | 1/1987 | United Kingdom | 2/406 |
| 8907923 | 9/1989 | World Int. Prop. O. | 604/396 |

Primary Examiner—Clifford D. Crowder
Assistant Examiner—Jeanette E. Chapman
Attorney, Agent, or Firm—Brooks & Kushman

[57] ABSTRACT

A disposable undergarment for releasably securing an absorbent pad in a pocket located in the crotch portion of the undergarment and a method for making the same is disclosed. The undergarment is made with a body portion and pocket portion. The pocket portion overlays the crotch portion and is attached to the body portion along a sufficient portion of its peripheral edge to form a pocket therebetween. The pocket is sufficient in size to secure or store an absorbent pad or the like. Preferably, the undergarment is made of an inexpensive material so that it may be disposable.

16 Claims, 2 Drawing Sheets fig-5 fig-6 fig-8 fig-7 fig-9

UNDERGARMENT WITH A POCKET FOR RELEASABLY SECURING AN ABSORBENT PAD

This is a continuation of copending application Ser. No. 07/653,623 filed on Jan. 11, 1991.

TECHNICAL FIELD

The present invention relates generally to undergarments, and in particular, to a disposable undergarment that has a pocket therein for releasably storing an absorbent pad, and a method for making the same.

BACKGROUND ART

Disposable undergarments or underpants are known in the art. Also known are reusable undergarments which releasably secure or store absorbent pads.

Some disposable undergarments are made strictly of a non-woven fabric, such as paper, while others also incorporate absorbent padding. Making undergarments of non-woven fabrics generally reduces the cost of manufacturing versus those made of expensive woven materials, i.e. cloth. Both the padded and unpadded undergarments often incorporate elasticized waist and leg openings to provide sealing around the waist and legs. Each type of disposable undergarment has distinct advantages and disadvantages.

The unpadded undergarments, made only of non-woven fabrics, have the advantage of being easily fabricated at a low cost, are very light-weight and comfortable, and can be compactly packaged to be easily carried or dispensed from a vending machine. However, these undergarments suffer the disadvantage of having very little absorbing capacity.

The padded undergarments have the advantage of providing absorption of relative large quantities of bodily fluids and wastes. Examples of such undergarments include baby diapers, which have absorbent liners, hygienic panties having absorbent pads for menstrual use and incontinence, and padded undergarments for use by persons suffering from incontinence, hemorrhoids, wound drainage, and the like.

The features of high-absorbency and disposability are highly desirable in light of such life-threatening diseases as AIDS (Acquired Immune Deficiency Syndrome) and hepatitis which are transmittable through body fluids and wastes. This is of particular concern among workers at institutions such as hospitals and corrections facilities where the occurrence of these diseases and the number of patients or inmates, respectively, are high.

These padded underpants or undergarments, while generally cheaper than cloth counterparts, are still more expensive and complex to manufacture than are the unpadded undergarments. Further, rather large boxes or containers are needed to package even a single pair of the padded undergarments.

Reusable undergarments, typically made of woven material such as a cotton fabric, are generally washed and used many times. Certain of these undergarments are designed to releasably secure absorbent pads. After use, the pads are discarded and the underpants cleaned. Often these underpants have means for securing the absorbent pad such that only the pad contacts the body and absorbs discharged fluids, thereby avoiding soiling of the underpants by the discharge.

A number of unpadded and padded disposable undergarments, as well as undergarments intended to be cleaned and reused and which releasably secure absorbent pads, are disclosed in U.S. patents.

Greene, U.S. Pat. No. 4,674,135, issued Jun. 23, 1987, discloses a disposable undergarment formed from a single sheet of non-woven cellulose material, but without a pocket. A crotch insert, also cut from the single sheet, is superposed and fixedly secured to a crotch portion for reinforcement, but is attached along its entire periphery.

Heren et al, U.S. Pat. No. 4,641,381 issued Feb. 10, 1987 and U.S. Pat. No. 4,646,362 issued Mar. 3, 1987, disclose an underpants which has front and rear panels, which are joined along side seams, and elasticized waist and leg openings. The underpants has three layers, an outer cover having an outer sub-layer of non-woven fibrous material and an inner sub-layer of impervious plastic material, a bodyside liner, and absorbent batt which is fixedly secured therebetween.

Ales et al, U.S. Pat. No. 4,642,819 issued Feb. 17, 1987, discloses a disposable panty having a bodyside liner, an outer cover, and an absorbent batt sandwiched therebetween. The absorbent batt may be attached to the outer cover, bodyside liner, or both.

Parravicini, U.S. Pat. No. 3,424,162 issued Jan. 28, 1969, discloses a disposable hygienic panty, made at least partially of cellulose material, having a portion that may incorporate a gauze insert sewn into the crotch portion, or else a complete gauze liner which is sewn to the body portion.

Steer, U.S. Pat. No. 4,695,279 issued Sep. 22, 1987, discloses reusable incontinence briefs and pants. A pocket, releasably securing an absorbent pad therein, is located in the crotch portion and is defined by an outer wall of a liquid-impervious material and an inner wall of like material having an oval hole therein.

Nathan, U.S. Pat. No. 4,928,323 issued May 29, 1990, discloses a reusable undergarment that has inner and outer, relative to a crotch portion, cooperating pocket panels for releasably securing to the ends of an absorbent pad. The pocket panels are longitudinally spaced from the center of the crotch portion.

Papajohn, U.S. Pat. No. 4,044,769 issued Aug. 30, 1977, discloses a reusable panty with a sanitary napkin. The absorbent napkin is releasably secured by two laterally spaced, overlapping portions, secured together by Velcro, having an opening therebetween for receiving discharged fluids.

Title, U.S. Pat. No. 2,985,170 issued May 23, 1961, discloses a reusable sanitary garment which has two longitudinally spaced, cooperating end pockets which receive the ends of an absorbent pad.

DISCLOSURE OF INVENTION

The present invention is an undergarment having a pocket for releasably securing or storing an absorbent pad therein. The undergarment comprises a pocket portion, having an outer periphery, and a body portion that is generally hour-glass shaped to partially form a pair of leg openings separated by a crotch portion, and two pairs of body sides. Each of the body sides is joined to form a waist opening and to complete the formation of the pair of leg openings. The pocket portion overlays the crotch portion and is attached to the body portion along a sufficient portion of its peripheral edge to form a pocket between the pocket portion and the body portion. The pocket portion may have an opening therein such that fluids may travel directly from the wearer to the pad without soiling the undergarment.

The pocket is designed to locate a pad where it is needed most, without providing unneeded absorbent protection elsewhere, such as is provided by underpants having full body liners. In the event the undergarment is to be used for women as a hygienic panty against menstrual flow or incontinence, the pocket may be made smaller and is located primarily only in the crotch portion. If used as a protective aid by men against incontinence, or if used as an aid against hemorrhoids, the pocket may extend further upwards towards the waist opening. With the pocket sized to snugly secure a pad, the pad may be placed in the front or the rear of the body portion or else in the crotch portion of the undergarment without movement.

This invention may be used both with and without the pad. In instances where no protection is needed, the underpants are worn like other underpants, the pocket portion providing some added protection. In the event more protection is necessary, a pad, preferably one commercially available, is inserted into the pocket.

The undergarment may be made of a low cost nonwoven material, is simple to manufacture, and therefore is cost competitive with other disposable unpadded underpants. The combined cost of the undergarment of this invention and a pad, when mass produced and competitively marketed, is cost-effective relative to an integrally padded disposable undergarment. The undergarment, as with pads, may be compactly packaged and sold through vending machines. The small size of the undergarment is also desirable for carrying in a purse or other luggage.

These undergarments are also ideally suited for institutional use. The undergarment is inexpensively manufactured and sold, thus may be economically disposed of after a single use, without significant handling by institutional personnel. Also, because the pad is releasably storable, only the undergarments of this invention need be carried in stock as they can meet the needs of both economical non-padded use and absorbent padded use when a pad is secured therein.

Accordingly, an object of the present invention is to provide an improved undergarment which is low-cost, lightweight, comfortably adapted to secure supplemental protection and which may be disposable.

Another object of the present invention is to provide an improved undergarment which, when used in conjunction with a pad stored or secured therein, has a large absorbency capacity that may be used by persons suffering from incontinence, hemorrhoids, menstruation, surgery, or any other condition resulting in bodily discharge in the pelvic region.

Still another object is provide an improved undergarment of two-piece construction that has a pocket for releasably securing an absorbent pad in an area where absorbency is needed without lining the entire undergarment with an absorbent material.

Yet another object is to provide an undergarment that may be compactly packaged and sold in small packages from vending machines, and is also easily carried in a purse or other compartment, and, if necessary, may be used in combination with a pad that may also be compactly packaged and is very readily available, which is particularly advantageous for travellers.

A more specific object is to provide an improved undergarment including the following features. First, the undergarment has a single-ply body portion configured initially in an hour-glass shape to partially form a pair of leg openings laterally spaced and separated by a crotch portion, and two pairs of body sides, each pair being longitudinally spaced. The undergarment also has a single ply pocket portion configured to fit between the leg openings and having a peripheral edge. Each pair of body sides is joined to form a waist opening and to complete the formation of the pair of leg openings. The relationship between the portions is such that the pocket portion overlays the crotch portion and is attached to the body portion along a sufficient portion of its peripheral edge to form a pocket between the pocket portion and the body portion of sufficient size to store an absorbent pad or the like.

Another more specific object is to provide a method for fabricating an undergarment including the following steps. First, providing a sheet-like single-ply material that is inexpensive yet strong and comfortable. Second, cutting from the material a single-ply body portion configured in an hour glass shape to partially form a pair of laterally spaced leg openings separated by a crotch portion, and two pairs of body sides, wherein each pair is longitudinally spaced. Third, cutting from the material a single-ply pocket portion configured to fit between the leg openings and having a peripheral edge. Fourth, joining each pair of body sides to form a waist opening and complete the pair of leg openings. And finally, overlaying the pocket portion on the crotch portion and attaching a sufficient portion of the pocket portion to the body portion to form a pocket between the pocket portion and the body portion of sufficient size to store an absorbent pad or the like. The fourth and fifth steps are interchangeable in order.

Other objects, features, and advantages will become more readily apparent from the following description and the accompanying sheets of drawings.

BEST MODES FOR CARRYING OUT THE INVENTION

The preferred embodiment of the present invention is an improved undergarment 10 comprising in two-piece construction a body portion 12 and a pocket portion 14, cut from a single-ply material. Preferably, the material is biodegradable and is an inexpensive, non-woven material made from cellulose, such as polyrayon, however, any comfortable, lightweight fabric that is of sufficient strength and low-cost may be used. It is contemplated that a washable and reusable material, possibly of several plys, such as a woven cotton material, could also be used.

Figure 1:
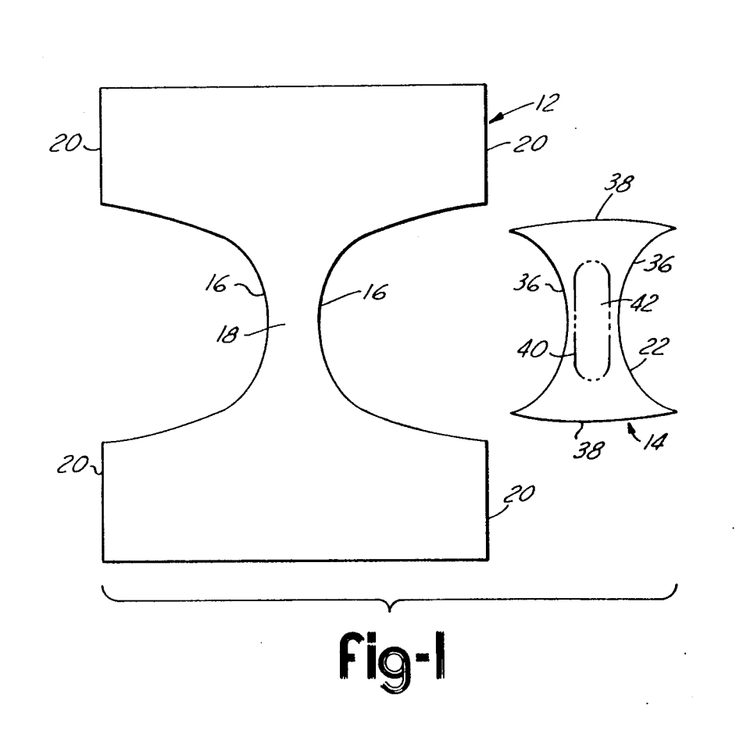
FIG. 1 is an exploded top view of the preferred embodiment of the present invention showing a body portion and a pocket portion of the undergarment prior to their attachment and showing in phantom line a variation in the pocket portion for this embodiment.

As shown in FIG. 1, undergarment 10 includes a single-ply body portion 12 configured initially in an hour-glass shape to partially form a pair of leg openings 16 laterally spaced and separated by a crotch portion 18, and two pairs of body sides 20, each pair being longitudinally spaced.

Also included is a single-ply pocket portion 14 configured to fit between the leg openings 16 and having a peripheral edge 22. Preferably, the peripheral edge 22 is generally rectangular having a pair of laterally spaced side edges 36 and a pair of longitudinally spaced transverse edges 38. Side edges 36, in the preferred embodiment, are generally configured to correspond to those of partially formed leg openings 16. The peripheral edge 22 also may be of shapes other than generally rectangular.

In an alternate version of this embodiment, pocket portion 14 may also have a perforation 40 such that material may be removed to create opening 42, or else, opening 42 may be pre-cut with the periphery 22. However, in the preferred embodiment pocket portion 14 does not include an opening 42.

Each pair of body sides 20 is joined to form a waist opening 24 and to complete the formation of the pair of leg openings 16. Preferably, this attachment is performed by sewing, however, other means for attachment such as with the use of adhesives or by other mechanical fastening means are also acceptable.

Pocket portion 14 is overlaid the crotch portion 18 and is attached to the body portion 12 along a sufficient portion of its peripheral edge 22 to form a pocket 28 between the pocket portion 14 and the body portion 12 of sufficient size to store an absorbent pad 30 or the like. In the preferred embodiment the body sides 20 are joined prior to attaching the pocket portion 14 to the body portion 12. It should be understood, however, that it also acceptable to attach pocket portion 14 to body portion 12 prior to the joining of body sides 20. The preferred means of attachment is by sewing, however, adhesive or other mechanical means for attachment may also be used. If opening 42 is present in pocket portion 14, it should be centrally located therein and of sufficient size to expose pad 30 or the like without being oversized allowing the pad to pass through the opening 42.

Figure 2:
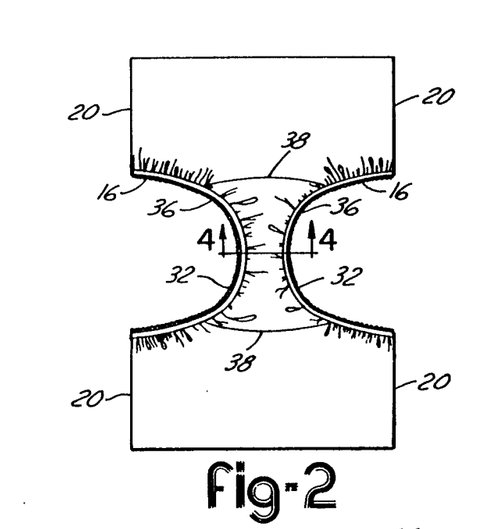
FIG. 2 is a top view of an intermediate combination of body and pocket portions showing the pocket portion attached along partially formed and elasticized leg openings.

In the preferred embodiment the waist opening 24 and the leg openings 16 are elasticized. FIG. 2 shows pocket portion 14 attaching to body portion 12, prior to the joining of body sides 20. Pocket portion 14 overlays crotch portion 18. Bands 32 of elastomeric material are then overlaid, stretched and attached to each of the side edges 36 of pocket portion 14 and the partially formed leg openings 16. To reduce costs, in the preferred embodiment, there is no folding over of the pocket portion 14 and the body portion 12 to form a hem about the bands 32. However, it is acceptable to hem these portions if so desired. Preferably, the attachment of the elastic band 32, pocket portion 14 and body portion 12 is by a sewn attachment.

Figure 3:
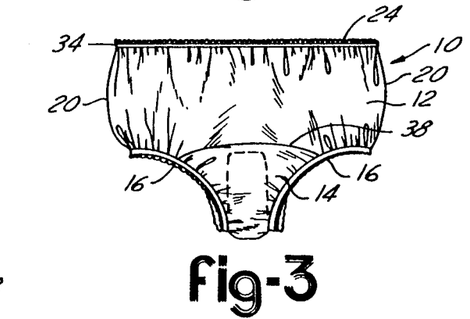
FIG. 3 is a front elevational view of a completed undergarment, turned inside out, showing the pocket portion attached to the elasticized leg openings and showing an elasticized waist opening.

FIG. 3 illustrates a completed undergarment 10, turned inside out for illustration purposes. A stretched band 34 of elastomeric material is attached to waist opening 24. Again the preferred method of attachment is by sewing with out forming a hem. With waist opening 24 and the leg openings 16 being elasticized, they are circumferentially constricted, enhancing their ability to conform the user's body and to retard leakage of fluid from undergarment 10.

Figure 4:
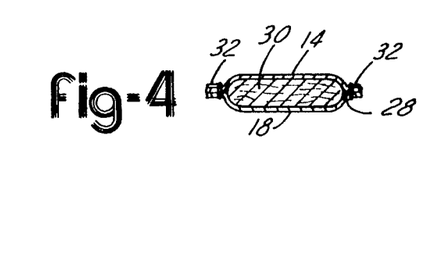
FIG. 4 is a sectional view taken along line 4—4 of FIG. 2 showing the attachment of body and pocket portions to an elastic band for elasticizing the leg openings and with a pad located within a pocket of the undergarment.
Figure 5:
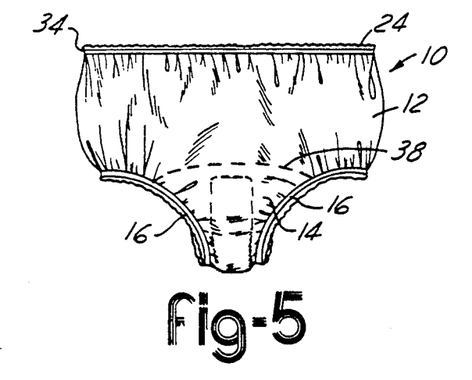
FIG. 5 is a rear elevational view of a completed undergarment, with an outline of the pad shown in phantom lines.

FIG. 4 is a sectional view taken along the longitudinal mid-section of crotch portion 18 showing pocket 28 formed between the pocket portion 14 and the crotch portion 18 of body portion 12. Inside pocket 28 is stored pad 30 or the like. Preferably pocket 28 is sized to snugly store pad 30 such that pad 30 does not move while being worn by a user. The pocket portion 14 is sized such that the maximum minimum width of pocket 28 is approximately 2.5" wide, which is about the width of many standard absorbent pads commercially sold. The pad may be a peripad, as used by hospitals or a standard sanitary napkin. The pocket 28 may even be smaller in cross-section than an unbounded pad 30 as absorbent pad 30 will freely conform to the shape of pocket 28. FIG. 5 shows a rear view of the undergarment 10, right side out.

In operation, in the preferred embodiment transverse edges 38 are unattached and an end of pad 30 is inserted between one transverse edge 38 and the body portion 12. Fingers are then inserted, between the other transverse edge 38 and the body portion 12, into pocket 28 grasping an end of absorbent pad 30 and pulling it into the desired location within pocket 28.

As seen in FIG. 5 in phantom lines, pocket 28 is wider at its ends than at its mid-length. The snug securement of pad 30 at the mid-length of pocket 28 prevents longitudinal movement even though snug securement may not be present proximate transverse edge 38.

If opening 42 is present, fluids may reach the pad 30 without soiling the undergarment.

When the wearer is through wearing the undergarment 10, the undergarment 10 is disposed. Alternatively, if the undergarment 10 is made of a more expensive, washable material, it possible to remove the absorbent pad 30, wash and reuse undergarment 10. Also, with the low cost construction of the present invention, the undergarment 10 may be economically used without pad 30 when absorption is not needed.

This first embodiment of the present invention, with the longitudinally relatively short pocket 28, located primarily in the crotch portion 18, as shown in FIGS. 4 and 5, is ideally suited for female use in conjunction with menstrual or incontinence conditions.

A second embodiment of this invention, shown in FIGS. 6–9, is more ideally suited for use by men suffering from incontinence and persons suffering with hemorrhoidal or other problems requiring protection more in the front or rear of the undergarment 10'. Its fabrication is similar to as that described above. However, preferably the pocket portion 14' is rectangular and extends longitudinally proximate the waist opening 24'. Again it is possible to have perforations 40' which assist in the removal of material in the central portion of pocket portion 14' to create opening 42' or else opening 42' may be pre-cut into pocket portion 14'.

Figure 8:
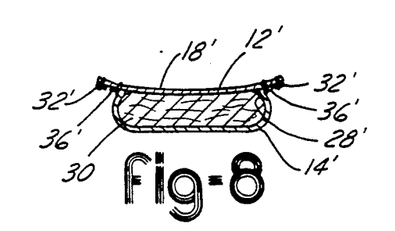
FIG. 8 is a sectional view of the second embodiment taken along the mid-length of the crotch portion with the undergarment inside out and a pad stored within a pocket.
Figure 9:
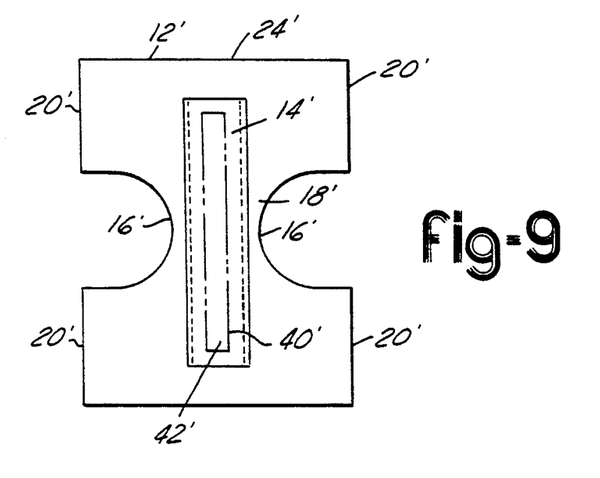
FIG. 9 is a top view of an intermediate combination prior to forming the undergarments of FIGS. 6 and 7 of the second embodiment showing an elongated pocket portion overlaying the body portion, wherein the pocket portion is generally rectangular and narrower than the crotch portion, and is attachable to the body portion between the leg openings.

Undergarments for men conventionally have a wider crotch portion 18' than do those for women, i.e. approximately 4" versus 2.5". To maintain the same snug securement or storage, as described above relative to a conventional absorbent pad 30, the pocket 28' is preferably again approximately 2.5" wide. Therefore, the pocket portion 14' will attach to the body portion 12' without attachment to leg openings 16'. FIG. 8 shows a pad 30 within pocket 28' taken along the mid-length of crotch portion 18'. The side edges 36' of pocket portion 28' resides within the attachment of bands 32' to leg openings 16'.

Figure 6:
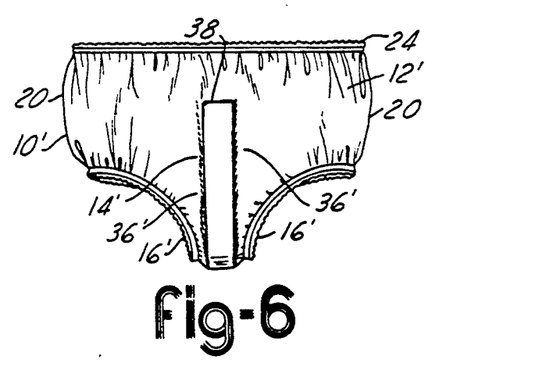
FIG. 6 is a front elevational view of a second embodiment of the present invention, turned inside out, wherein the pocket extends proximate the waist opening and has a pad located in the front of the undergarment.
Figure 7:
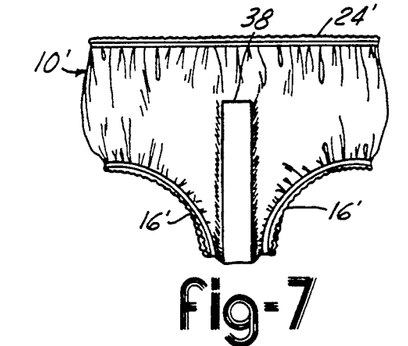
FIG. 7 is a rear elevational view of the second embodiment, turned inside out, showing a pad located in the rear of the undergarment.

A pad 30 may be stored securely in the front, rear, or any portion therebetween of pocket 28' to accommodate absorption where needed. FIGS. 6 and 7, respectively, show a pad located in the front and rear of undergarment 10'.

The preferred method of fabricating the improved undergarment 10 of the present invention includes the following steps.

First, a sheet-like single-ply material is provided.

Second, from the material is cut a single-ply body portion 12 configured in an hour-glass shape to partially form a pair of laterally spaced leg openings 16 separated by a crotch portion 18, and two pairs of body sides 20, each pair being longitudinally spaced and also cut from the material is a single-ply pocket portion 14 configured to fit between the leg openings 16 and having a peripheral edge 22.

The next step is joining each pair of body sides 20 to form a waist opening 24 and to complete the pair of leg openings 16.

The final step is overlaying the pocket portion 14 on the crotch portion 18 and attaching a sufficient portion of the peripheral edge 22 of the pocket portion 14 to the body portion 12 to form a pocket 28 between the pocket portion 14 and the body portion 12 of sufficient size to store an absorbent pad 30 or the like.

While the above described steps are in their order of preference, the last two steps are interchangeable.

Additionally, the openings may be elasticized by adding the step of overlaying stretched bands 32 and 34 of elastomeric material over the leg and waist openings, respectively, and attaching bands 32 and 34 to the openings such that the leg and waist openings 16 and 24 are circumferentially constricted when the bands 32 and 34 are not stretched. When the pocket portion 14 is being attached to the leg openings 16, as in the first preferred embodiment, the bands 32 should also be attached at that time.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. An improved undergarment comprising:
a body portion configured initially in an hour-glass shape to partially form a pair of leg openings laterally spaced and separated by a crotch portion, and two pairs of body sides, each pair being longitudinally spaced;
a one piece pocket portion sized to be substantially coextensive with a standard sanitary napkin and configured to fit between said leg openings and having a peripheral edge defined by a pair of longitudinally spaced transverse edges and a pair of laterally spaced side edges;
each pair of body sides being joined to form a waist opening and complete the formation of the pair of leg openings; and
said pocket portion overlaying said crotch portion and being attached to the body portion along the side edges to form a pocket and a pair of longitudinally spaced openings between the pocket portion and the body portion so that a user's fingers may be inserted within either one of the openings to grasp an end of the sanitary napkin and pull the sanitary napkin through the other opening and into a desired location within the pocket.

2. An improved undergarment comprising:
a body portion having a pair of leg openings laterally spaced and separated by a crotch portion, and a waist opening; and
a pocket portion configured to fit between said leg openings and having a peripheral edge with a pair of longitudinally spaced transverse edges and a pair of laterally paced side edges;
said pocket portion overlaying said crotch portion and being attached to the body portion along the side edges to form a pocket and a pair of longitudinally spaced openings between the pocket portion and the body portion so that a user's fingers may be inserted within either one of the openings to grasp an end of the sanitary napkin and pull the sanitary napkin through the other opening and into a desired location within the pocket.

3. The improved undergarment of claim 2 wherein the body portion and pocket portion are a single-ply.

4. The improved undergarment of claim 2 further comprising initially stretched bands of elastomeric material attached to each of said leg and waist openings such that said leg and waist openings are circumferentially constricted when said band of elastomeric material is not stretched.

5. The improved undergarment of claim 4 wherein the band of elastomeric material overlays the pocket portion and the body portion and the attachment of said band to said portions is without either the pocket portion or the body portion folding over the band.

6. The improved undergarment of claim 2 wherein the pocket portion is elongated to form an elongated pocket when attached to the body portion wherein at least one end of the pocket portion extends longitudinally and terminates proximate the waist opening.

7. The improved undergarment of claim 6 wherein the pocket is elongated sufficiently to permit positioning of the sanitary napkin in at least one of the rear or the front of the undergarment.

8. The improved undergarment of claim 2 wherein said pocket portion is attached to said crotch portion along said leg openings.

9. The improved undergarment of claim 2 wherein the body portion and the pocket portion are made of a non-woven fabric, whereby to be inexpensive and disposable.

10. The improved undergarment of claim 9 wherein the fabric is made of a cellulose material.

11. The improved undergarment of claim 9 wherein the fabric is made of polyrayon.

12. The improved undergarment of claim 2 wherein the pocket portion has an opening located centrally therein and of sufficient size to expose said pad or the like.

13. The improved undergarment of claim 2 wherein the pocket formed between said pocket portion and said body portion is configured in an hour-glass shape.

14. The improved undergarment of claim 2 wherein:
said pocket has a centrally located region bounded by a series of perforation whereby the centrally located region may be removed from the pocket portion to expose the pocket to the user.

15. An improved undergarment comprising:
a body portion having a pair of leg openings laterally spaced and separated by a crotch portion, and two laterally spaced pairs of body sides, each pair being longitudinally spaced;
a single piece pocket portion configured in an hourglass shape and sized to be substantially coextensive with a standard sanitary napkin and sized to fit between said leg openings and having a peripheral edge which includes a pair of laterally spaced side edges and a pair of longitudinally spaced transverse edges;
each pair of body sides being joined to form a waist opening and complete the formation of the pair of leg openings; and
said pocket portion overlaying said crotch portion and being attached to the body portion along said laterally spaced side edges to form a pocket with a pair of longitudinally spaced openings between said pocket portion and said body portion, both transverse edges being free of attachment and of sufficient length to allow easy insertion of the sanitary napkin into either opening of the pocket with the side edges sufficiently laterally spaced from one another adjacent the crotch portion to snugly store the sanitary napkin with the pocket.

16. The undergarment of claim 15 wherein a portion of the pocket is smaller in cross-section than an unbound standard sanitary napkin such that when the sanitary napkin is inserted therein, the sanitary napkin will conform to the shape of the pocket securely retaining the sanitary napkin.

* * * * *

UNITED STATES PATENT AND TRADEMARK OFFICE
CERTIFICATE OF CORRECTION

PATENT NO. : 5,325,543
DATED : July 5, 1994
INVENTOR(S) : Tanya R. Allen

It is certified that error appears in the above-indentified patent and that said Letters Patent is hereby corrected as shown below:

Column 8, Line 9, Claim 1 after "with a" delete "standard", and after "napkin" insert --of a predetermined size--;

Column 8, Line 19, Claim 1 after "pair of" insert --sufficiently--;

Column 8, Line 21, Claim 1 after "may be" insert -- easily --.

Column 8, Line 24, Claim 1 after "napkin" insert --sufficiently--;

Column 8, Line 25, Claim 1 delete "location" and insert --position--;

UNITED STATES PATENT AND TRADEMARK OFFICE
CERTIFICATE OF CORRECTION

PATENT NO. : 5,325,543
DATED : July 5, 1994
INVENTOR(S) : Tanya R. Allen

It is certified that error appears in the above-indentified patent and that said Letters Patent is hereby corrected as shown below:

Column 8, Line 25, Claim 1 after "pocket" insert --with the ends of the sanitary napkin being restrained by the pocket to prevent relative movement between the sanitary napkin and the pocket when the undergarment is worn by a user--;

Column 10, Line 1, Claim 15 delete "standard" and after "napkin" insert --of a predetermined size--;

Column 10, Line 19, Claim 15 after "pocket" insert --with the ends of the sanitary napkin being restrained by the pocket to prevent relative movement between the sanitary napkin and the undergarment when worn by a user--;

Column 8, Line 26, Claim 2 after "undergarment" insert --for holding an elongated absorbent pad of a predetermined size, the undergarment--;

UNITED STATES PATENT AND TRADEMARK OFFICE
CERTIFICATE OF CORRECTION

PATENT NO. : 5,325,543
DATED : July 5, 1994
INVENTOR(S) : Tanya R. Allen

It is certified that error appears in the above-indentified patent and that said Letters Patent is hereby corrected as shown below:

Column 8, Line 33, Claim 2

26), after "edges" insert --, said pocket being sufficiently sized to completely cover the absorbent pad--;

Column 8, Line 42, Claim 2 delete "location" and insert --position--;

Column 8, Line 42, Claim 2 after "pocket" insert with the end of the sanitary napkin being restrained by the pocket to prevent relative movement between the sanitary napkin and the undergarment when worn by a user--.

Signed and Sealed this

Twenty-seventh Day of June, 1995

Attest:

BRUCE LEHMAN

Attesting Officer

Commissioner of Patents and Trademarks